# (12) United States Patent
Miller

(10) Patent No.: US 9,078,727 B2
(45) Date of Patent: Jul. 14, 2015

(54) SYSTEM AND METHOD FOR TREATING TISSUE WALL PROLAPSE

(75) Inventor: Dennis Miller, Shorewood, WI (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 944 days.

(21) Appl. No.: 11/686,683

(22) Filed: Mar. 15, 2007

(65) Prior Publication Data

US 2007/0270890 A1 Nov. 22, 2007

Related U.S. Application Data

(60) Provisional application No. 60/782,911, filed on Mar. 16, 2006, provisional application No. 60/852,932, filed on Oct. 19, 2006.

(51) Int. Cl.
| | |
|---|---|
| A61F 2/00 | (2006.01) |
| A61B 17/04 | (2006.01) |
| A61B 17/062 | (2006.01) |
| A61B 17/00 | (2006.01) |
| A61B 17/06 | (2006.01) |

(52) U.S. Cl.
CPC ........... *A61F 2/0045* (2013.01); *A61B 17/0469* (2013.01); *A61B 17/0482* (2013.01); *A61B 17/0625* (2013.01); *A61F 2/0063* (2013.01); *A61B 2017/00805* (2013.01); *A61B 2017/06028* (2013.01); *A61F 2250/0023* (2013.01)

(58) Field of Classification Search
CPC ... A61F 2/0004; A61F 2/0031; A61F 2/0036; A61F 2/0045; A61F 2/0063
USPC .............. 600/29–32, 37; 128/DIG. 25; 606/151–157
See application file for complete search history.

(56) References Cited

U.S. PATENT DOCUMENTS

| 669,034 A | 2/1901 | Manly |
|---|---|---|
| 2,687,131 A | 8/1954 | Raiche |
| 3,123,077 A | 3/1964 | Alcamo |
| 4,083,369 A | 4/1978 | Sinnreich |

(Continued)

FOREIGN PATENT DOCUMENTS

| EP | 0088714 A1 | 9/1983 |
|---|---|---|
| EP | 0141589 A1 | 5/1985 |

(Continued)

OTHER PUBLICATIONS

International Search Report dated Aug. 28, 2007 issued in PCT/US2007/064079; 4 pages.

(Continued)

*Primary Examiner* — Charles A. Marmor, II
*Assistant Examiner* — Carrie R Dorna

(57) ABSTRACT

The invention disclosed herein includes an apparatus and a method for treatment of vaginal prolapse conditions. The apparatus is a graft having a central body portion with at least one strap extending from it. The strap has a bullet needle attached to its end portion and is anchorable to anchoring tissue in the body of a patient. The invention makes use of a delivery device adapted to deploy the graft in a patient. The inventive method includes the steps of making an incision in the vaginal wall of a patient, opening the incision to gain access inside the vagina and pelvic floor area, inserting the inventive apparatus through the incision, and attaching the straps of the apparatus to anchoring tissue in the patient.

37 Claims, 7 Drawing Sheets

(56) References Cited

U.S. PATENT DOCUMENTS

| | | |
|---|---|---|
| 4,324,331 A | 4/1982 | Ignasiak |
| 4,792,336 A | 12/1988 | Hlavacek et al. |
| 4,919,667 A | 4/1990 | Richmond |
| 4,979,956 A | 12/1990 | Silvestrini |
| 4,998,912 A | 3/1991 | Scarbrough et al. |
| 5,013,292 A | 5/1991 | Lemay |
| 5,082,112 A | 1/1992 | Dunklee |
| 5,112,344 A | 5/1992 | Petros |
| 5,149,329 A | 9/1992 | Richardson |
| 5,217,466 A | 6/1993 | Hasson |
| 5,217,486 A | 6/1993 | Rice et al. |
| 5,217,494 A | 6/1993 | Coggins et al. |
| 5,263,969 A | 11/1993 | Phillips |
| 5,356,432 A | 10/1994 | Rutkow et al. |
| 5,362,294 A | 11/1994 | Seitzinger |
| 5,364,408 A | 11/1994 | Gordon |
| 5,383,905 A | 1/1995 | Golds et al. |
| 5,405,359 A | 4/1995 | Pierce |
| 5,425,747 A | 6/1995 | Brotz |
| 5,451,235 A | 9/1995 | Lock et al. |
| 5,458,609 A | 10/1995 | Gordon et al. |
| 5,458,636 A | 10/1995 | Brancato |
| 5,464,409 A | 11/1995 | Mohajer |
| 5,485,917 A | 1/1996 | Early |
| 5,527,341 A | 6/1996 | Gogolewski et al. |
| 5,534,008 A | 7/1996 | Acksel |
| 5,540,704 A | 7/1996 | Gordon et al. |
| 5,562,689 A | 10/1996 | Green et al. |
| 5,569,283 A | 10/1996 | Green et al. |
| 5,575,800 A | 11/1996 | Gordon |
| 5,578,044 A | 11/1996 | Gordon et al. |
| 5,584,859 A | 12/1996 | Brotz |
| 5,611,515 A | 3/1997 | Benderev et al. |
| 5,643,311 A | 7/1997 | Smith et al. |
| 5,662,664 A | 9/1997 | Gordon et al. |
| 5,683,402 A | 11/1997 | Cosgrove et al. |
| 5,700,272 A | 12/1997 | Gordon et al. |
| 5,702,397 A | 12/1997 | Goble et al. |
| 5,713,910 A | 2/1998 | Gordon et al. |
| 5,720,761 A | 2/1998 | Kaali |
| 5,741,277 A | 4/1998 | Gordon et al. |
| 5,741,279 A | 4/1998 | Gordon et al. |
| 5,741,299 A | 4/1998 | Rudt |
| 5,840,011 A | 11/1998 | Landgrebe et al. |
| 5,871,488 A | 2/1999 | Tovey et al. |
| 5,899,909 A | 5/1999 | Claren et al. |
| 5,922,826 A | 7/1999 | Kuze et al. |
| 5,931,855 A | 8/1999 | Buncke |
| 5,948,001 A | 9/1999 | Larsen |
| 5,976,127 A | 11/1999 | Lax |
| 5,988,549 A | 11/1999 | Hitomi et al. |
| 6,010,447 A | 1/2000 | Kardjian |
| 6,012,580 A | 1/2000 | Peters et al. |
| 6,039,686 A | 3/2000 | Kovac |
| 6,042,534 A * | 3/2000 | Gellman et al. ............... 600/30 |
| 6,042,536 A | 3/2000 | Tihon et al. |
| 6,042,592 A | 3/2000 | Schmitt |
| 6,044,847 A | 4/2000 | Carter et al. |
| 6,048,351 A | 4/2000 | Gordon et al. |
| 6,096,051 A | 8/2000 | Kortenbach et al. |
| 6,102,921 A | 8/2000 | Zhu et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,224,616 B1 | 5/2001 | Kugel |
| 6,267,772 B1 | 7/2001 | Mulhauser et al. |
| 6,273,852 B1 * | 8/2001 | Lehe et al. ............... 600/30 |
| 6,306,079 B1 | 10/2001 | Trabucco |
| 6,322,492 B1 | 11/2001 | Kovac |
| 6,328,686 B1 | 12/2001 | Kovac |
| 6,346,111 B1 | 2/2002 | Gordon et al. |
| 6,375,662 B1 | 4/2002 | Schmitt |
| 6,382,214 B1 | 5/2002 | Raz et al. |
| 6,406,423 B1 | 6/2002 | Scetbon |
| 6,454,778 B2 | 9/2002 | Kortenbach |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,547,800 B2 | 4/2003 | Foerster et al. |
| 6,551,329 B1 | 4/2003 | Kortenbach et al. |
| 6,565,580 B1 | 5/2003 | Beretta |
| 6,575,897 B1 | 6/2003 | Ory et al. |
| 6,575,998 B2 | 6/2003 | Beyar |
| 6,582,443 B2 | 6/2003 | Cabak et al. |
| 6,592,515 B2 | 7/2003 | Thierfelder et al. |
| 6,592,610 B2 | 7/2003 | Beyar et al. |
| 6,595,911 B2 | 7/2003 | LoVuolo |
| 6,596,001 B2 | 7/2003 | Stormby et al. |
| 6,599,235 B2 | 7/2003 | Kovac |
| 6,599,310 B2 | 7/2003 | Leung et al. |
| 6,612,977 B2 | 9/2003 | Staskin et al. |
| 6,638,209 B2 | 10/2003 | Landgrebe |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau et al. |
| 6,648,899 B2 | 11/2003 | Kalinski et al. |
| 6,648,921 B2 | 11/2003 | Anderson et al. |
| 6,652,450 B2 | 11/2003 | Neisz et al. |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,691,711 B2 | 2/2004 | Raz et al. |
| 6,695,855 B1 | 2/2004 | Gaston |
| 6,702,827 B1 | 3/2004 | Lund et al. |
| 6,730,110 B1 | 5/2004 | Harari et al. |
| 6,746,455 B2 | 6/2004 | Beyar et al. |
| 6,752,814 B2 | 6/2004 | Gellman et al. |
| 6,755,781 B2 | 6/2004 | Gellman |
| 6,808,487 B2 | 10/2004 | Migliari |
| 6,830,052 B2 | 12/2004 | Carter et al. |
| 6,848,152 B2 | 2/2005 | Genova et al. |
| 6,872,227 B2 | 3/2005 | Sump et al. |
| 6,881,184 B2 | 4/2005 | Zappala |
| 6,890,338 B1 | 5/2005 | Davis et al. |
| 6,908,425 B2 | 6/2005 | Luscombe |
| 6,911,003 B2 | 6/2005 | Anderson et al. |
| 6,911,034 B2 | 6/2005 | Nobles et al. |
| 6,932,759 B2 | 8/2005 | Kammerer et al. |
| 6,936,052 B2 | 8/2005 | Gellman et al. |
| 6,936,054 B2 | 8/2005 | Chu |
| 6,936,952 B2 | 8/2005 | Takamine |
| 6,946,003 B1 | 9/2005 | Wolowacz et al. |
| 6,953,428 B2 | 10/2005 | Gellman et al. |
| 6,960,160 B2 | 11/2005 | Browning |
| 6,971,986 B2 | 12/2005 | Staskin et al. |
| 6,986,780 B2 | 1/2006 | Rudnick et al. |
| 6,991,597 B2 | 1/2006 | Gellman et al. |
| 7,011,688 B2 | 3/2006 | Gryska et al. |
| 7,025,772 B2 | 4/2006 | Gellman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 | 8/2006 | Tannhauser |
| 7,090,686 B2 | 8/2006 | Nobles et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,122,039 B2 | 10/2006 | Chu |
| 7,131,943 B2 | 11/2006 | Kammerer |
| 7,131,944 B2 | 11/2006 | Jacquetin |
| 7,198,597 B2 | 4/2007 | Siegel et al. |
| 7,204,801 B2 | 4/2007 | Grocela |
| 7,204,802 B2 | 4/2007 | De Leval |
| 7,223,229 B2 | 5/2007 | Inman et al. |
| 7,226,407 B2 | 6/2007 | Kammerer et al. |
| 7,226,408 B2 | 6/2007 | Harai et al. |

(56) References Cited

U.S. PATENT DOCUMENTS

| | | |
|---|---|---|
| 7,229,453 B2 | 6/2007 | Anderson et al. |
| 7,235,043 B2 | 6/2007 | Gellman et al. |
| 7,244,260 B2 | 7/2007 | Koseki |
| 7,244,759 B2 | 7/2007 | Mulle et al. |
| 7,267,645 B2 | 9/2007 | Anderson et al. |
| 7,291,104 B2 | 11/2007 | Neisz et al. |
| 7,351,197 B2 | 4/2008 | Montpetit et al. |
| 7,361,138 B2 | 4/2008 | Wagner et al. |
| 7,364,541 B2 | 4/2008 | Chu et al. |
| 7,402,133 B2 | 7/2008 | Chu et al. |
| 7,413,540 B2 | 8/2008 | Gellman et al. |
| 7,527,588 B2 | 5/2009 | Zaddem et al. |
| 8,128,552 B2 | 3/2012 | O'Donnell |
| 2001/0023356 A1 | 9/2001 | Raz et al. |
| 2001/0049467 A1 | 12/2001 | Lehe et al. |
| 2002/0010457 A1 | 1/2002 | Duchon et al. |
| 2002/0028980 A1 | 3/2002 | Thierfelder et al. |
| 2002/0099259 A1* | 7/2002 | Anderson et al. ............... 600/29 |
| 2002/0128670 A1 | 9/2002 | Ulmsten et al. |
| 2002/0133236 A1 | 9/2002 | Rousseau |
| 2002/0143234 A1 | 10/2002 | LoVuolo |
| 2002/0147382 A1 | 10/2002 | Neisz et al. |
| 2002/0151909 A1 | 10/2002 | Gellman et al. |
| 2002/0156489 A1 | 10/2002 | Gellman et al. |
| 2003/0009181 A1 | 1/2003 | Gellman et al. |
| 2003/0023138 A1 | 1/2003 | Luscombe |
| 2003/0023250 A1 | 1/2003 | Watschke et al. |
| 2003/0055313 A1 | 3/2003 | Anderson et al. |
| 2003/0078604 A1 | 4/2003 | Walshe |
| 2003/0125715 A1 | 7/2003 | Kuehn et al. |
| 2003/0149334 A1 | 8/2003 | Ulmsten et al. |
| 2003/0176762 A1 | 9/2003 | Kammerer |
| 2003/0191360 A1 | 10/2003 | Browning |
| 2003/0208208 A1 | 11/2003 | Chu |
| 2003/0220538 A1 | 11/2003 | Jacquetin |
| 2003/0225424 A1 | 12/2003 | Benderev |
| 2003/0233107 A1 | 12/2003 | Gellman et al. |
| 2003/0233108 A1 | 12/2003 | Gellman et al. |
| 2004/0006353 A1 | 1/2004 | Bosley et al. |
| 2004/0015048 A1 | 1/2004 | Neisz et al. |
| 2004/0015177 A1 | 1/2004 | Chu |
| 2004/0034372 A1 | 2/2004 | Chu |
| 2004/0039246 A1 | 2/2004 | Gellman et al. |
| 2004/0039453 A1 | 2/2004 | Anderson et al. |
| 2004/0059293 A1 | 3/2004 | Chu et al. |
| 2004/0068159 A1 | 4/2004 | Neisz et al. |
| 2004/0073234 A1 | 4/2004 | Chu et al. |
| 2004/0087970 A1 | 5/2004 | Chu et al. |
| 2004/0106847 A1 | 6/2004 | Benderev |
| 2004/0116944 A1 | 6/2004 | Chu et al. |
| 2004/0133217 A1 | 7/2004 | Watschke |
| 2004/0138747 A1 | 7/2004 | Kaladelfos |
| 2004/0181243 A1 | 9/2004 | Chu et al. |
| 2004/0186515 A1 | 9/2004 | Rosenblatt |
| 2004/0225181 A1 | 11/2004 | Chu et al. |
| 2004/0230206 A1 | 11/2004 | Gellman et al. |
| 2004/0231678 A1 | 11/2004 | Fierro |
| 2004/0236356 A1 | 11/2004 | Rioux et al. |
| 2004/0249397 A1 | 12/2004 | Delorme et al. |
| 2004/0249473 A1 | 12/2004 | Delorme et al. |
| 2005/0004427 A1 | 1/2005 | Cervigni |
| 2005/0004576 A1 | 1/2005 | Benderev |
| 2005/0038451 A1 | 2/2005 | Rao et al. |
| 2005/0038452 A1 | 2/2005 | Chu |
| 2005/0075660 A1 | 4/2005 | Chu et al. |
| 2005/0080317 A1 | 4/2005 | Merade |
| 2005/0090706 A1 | 4/2005 | Gellman et al. |
| 2005/0096499 A1 | 5/2005 | Li et al. |
| 2005/0101834 A1 | 5/2005 | Merade |
| 2005/0107805 A1 | 5/2005 | Bouffier et al. |
| 2005/0131391 A1 | 6/2005 | Chu et al. |
| 2005/0131392 A1 | 6/2005 | Chu et al. |
| 2005/0131393 A1 | 6/2005 | Chu et al. |
| 2005/0177022 A1 | 8/2005 | Chu et al. |
| 2005/0192600 A1 | 9/2005 | Nicolo et al. |
| 2005/0222589 A1 | 10/2005 | Chu |
| 2005/0222591 A1 | 10/2005 | Gingras et al. |
| 2005/0234291 A1 | 10/2005 | Gingras |
| 2005/0245787 A1 | 11/2005 | Cox et al. |
| 2005/0250977 A1 | 11/2005 | Montpetit et al. |
| 2005/0250978 A1 | 11/2005 | Kammerer |
| 2005/0256366 A1 | 11/2005 | Chu |
| 2005/0256530 A1 | 11/2005 | Petros |
| 2005/0261545 A1 | 11/2005 | Gellman et al. |
| 2005/0261547 A1 | 11/2005 | Bouffier |
| 2005/0277807 A1 | 12/2005 | MacLean et al. |
| 2005/0278037 A1 | 12/2005 | Delorme et al. |
| 2006/0015001 A1 | 1/2006 | Staskin et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0041263 A1 | 2/2006 | Chu et al. |
| 2006/0052801 A1 | 3/2006 | Dreyfuss et al. |
| 2006/0058574 A1 | 3/2006 | Priewe et al. |
| 2006/0058575 A1 | 3/2006 | Zaddem et al. |
| 2006/0069301 A1 | 3/2006 | Neisz et al. |
| 2006/0089524 A1 | 4/2006 | Chu |
| 2006/0089525 A1 | 4/2006 | Mamo et al. |
| 2006/0122457 A1 | 6/2006 | Kovac et al. |
| 2006/0173237 A1 | 8/2006 | Jacquetin |
| 2006/0205995 A1 | 9/2006 | Browning |
| 2006/0211911 A1 | 9/2006 | Jao et al. |
| 2006/0229493 A1 | 10/2006 | Weiser et al. |
| 2006/0229596 A1 | 10/2006 | Weiser et al. |
| 2006/0264698 A1 | 11/2006 | Kondonis et al. |
| 2007/0043255 A1 | 2/2007 | O'Donnell |
| 2007/0055095 A1 | 3/2007 | Chu et al. |
| 2007/0161849 A1 | 7/2007 | Goldberg et al. |
| 2007/0173864 A1* | 7/2007 | Chu ............................ 606/139 |
| 2007/0276358 A1 | 11/2007 | Barzell et al. |
| 2008/0177132 A1 | 7/2008 | Alinsod et al. |
| 2008/0234543 A1 | 9/2008 | Goldwasser |
| 2009/0171140 A1 | 7/2009 | Chu |
| 2009/0171142 A1 | 7/2009 | Chu |
| 2009/0171143 A1 | 7/2009 | Chu et al. |
| 2010/0152530 A1 | 6/2010 | Timmer et al. |
| 2011/0098527 A1 | 4/2011 | Goldberg |
| 2012/0059217 A1 | 3/2012 | Goldberg et al. |

FOREIGN PATENT DOCUMENTS

| | | |
|---|---|---|
| EP | 0299158 A1 | 1/1989 |
| EP | 0362146 A1 | 4/1990 |
| EP | 0412664 A1 | 2/1991 |
| EP | 0567130 A1 | 10/1993 |
| EP | 1201189 A2 | 5/2002 |
| EP | 1508305 A2 | 2/2005 |
| EP | 1520554 A2 | 4/2005 |
| EP | 1609439 A1 | 6/2005 |
| EP | 1933786 A2 | 6/2008 |
| EP | 2617385 A2 | 7/2013 |
| EP | 1998711 B1 | 12/2013 |
| FR | 2852817 A1 | 3/2003 |
| FR | 2871365 A1 | 6/2004 |
| FR | 2852818 A1 | 10/2004 |
| GB | 670349 | 4/1952 |
| JP | 06114067 A2 | 4/1994 |
| JP | 8033635 A | 2/1996 |
| JP | 08117239 A2 | 5/1996 |
| JP | 2003-523786 A | 8/2003 |
| JP | 2004-524836 | 8/2004 |
| JP | 2004-526483 A | 9/2004 |
| MX | PA04008407 A | 8/2004 |
| WO | 96/09796 A2 | 4/1996 |
| WO | 96/39948 A1 | 12/1996 |
| WO | 98/43545 A1 | 3/1998 |
| WO | 98/35616 A1 | 8/1998 |
| WO | 99/37216 A1 | 7/1999 |
| WO | 00/74594 A1 | 12/2000 |
| WO | 00/74613 A1 | 12/2000 |
| WO | 0232284 A2 | 4/2002 |
| WO | WO 02/31681 | 4/2002 |
| WO | 02/062237 A1 | 8/2002 |
| WO | 02/078571 A2 | 10/2002 |

(56) References Cited

FOREIGN PATENT DOCUMENTS

| WO | 03/092546 A3 | 11/2003 | | |
|---|---|---|---|---|
| WO | 2004/001619 A1 | 12/2003 | | |
| WO | WO2004012626 | * | 2/2004 | ............... A61F 2/00 |
| WO | 2004045457 A1 | 6/2004 | | |
| WO | WO 2004/091442 A2 | 10/2004 | | |
| WO | WO 2004/091443 A2 | 10/2004 | | |
| WO | 2005/051204 A1 | 6/2005 | | |
| WO | 2005/122721 A2 | 12/2005 | | |
| WO | 2005/122954 A1 | 12/2005 | | |
| WO | 2006/015031 A2 | 2/2006 | | |
| WO | 2006/046950 A1 | 5/2006 | | |
| WO | 2007/019374 A2 | 2/2007 | | |
| WO | 2007014240 A1 | 2/2007 | | |
| WO | 2007016698 A3 | 2/2007 | | |
| WO | 2007/059199 A2 | 5/2007 | | |
| WO | 2007087132 A1 | 8/2007 | | |
| WO | 2007/109508 A1 | 9/2007 | | |
| WO | 2009038781 A1 | 3/2009 | | |
| WO | 2009102945 A2 | 8/2009 | | |
| WO | 2012030834 A2 | 3/2012 | | |
| WO | 2012030834 A3 | 3/2012 | | |

OTHER PUBLICATIONS

Office Action received for EP Application No. 07716311.1, mailed on Dec. 8, 2009, 3 pages.
International Search Report for PCT Application No. PCT/US2007/000190, mailed on Jul. 24, 2008, 5 pages.
Partial European Search Report for EP Patent Application No. EP 01117717, mailed on Apr. 18, 2007, 5 pages.
Search Report received or European Patent Application No. EP 90307704, mailed on Apr. 18, 2007, 1 page.
International Search Report for PCT Application No. PCT/US2004/035329, mailed on Jul. 6, 2005, 7 pages.
International Search Report for International Application No. PCT/AU2004/001674, mailed on Dec. 21, 2004, 3 pages.
International Search Report for PCT Application No. PCT/US2005/021267, mailed on Nov. 30, 2005, 6 pages.
International Search Report for PCT Application No. PCT/US1998/03066, mailed on May 28, 1998, 2 pages.
"Capio® Suture Capturing Devices", Reach, Throw and Capture: One Step. One Device., Boston Scientific, 2005, 4 pages.
"CapioTM CL Transvaginal Suture Capturing Device", Transvaginal Suture Fixation to Cooper's Ligament for Sling Procedures, Boston Scientific, 2000, 4 pages.
Response to Office Action received for U.S. Appl. No. 11/331,777, filed on Aug. 5, 2009, 7 pages.
Office Action received for U.S. Appl. No. 11/535,901, mailed on Jun. 9, 2009, 22 pages.
Response to Office Action received for U.S. Appl. No. 11/331,777, filed on Jul. 15, 2008, 8 pages.
Response to Office Action received for U.S. Appl. No. 11/535,901, filed on Oct. 9, 2009. 12 pages.
Office Action received for U.S. Appl. No. 11/331,777, mailed on Dec. 8, 2009, 16 pages.
Office Action received for U.S. Appl. No. 11/331,777, mailed on Oct. 14, 2008, 13 pages.
Response to Restriction Requirement for U.S. Appl. No. 11/535,901, filed on May 14, 2009, 2 pages.
Advisory Action received for U.S. Appl. No. 11/331,777, mailed on Feb. 17, 2010, 3 pages.
Advisory Action received for U.S. Appl. No. 11/331,777, mailed on Mar. 10, 2009, 3 pages.
Response to Office Action received for U.S. Appl. No. 11/331,777, filed on Dec. 11, 2008, 8 pages.
Office Action received for U.S. Appl. No. 11/331,777, mailed on Apr. 21, 2008, 14 pages.
Office Action received for U.S. Appl. No. 11/331,777, mailed on May 8, 2009, 14 pages.
Office Action received for U.S. Appl. No. 11/535,901, mailed on Jan. 29, 2009, 22 pages.
Response to Advisory Action received for U.S. Appl. No. 11/331,777, filed on Mar. 16, 2009, 10 pages.
Response to Office Action received for U.S. Appl. No. 11/331,777, filed on Feb. 5, 2010, 8 pages.
Restriction Requirement received for U.S. Appl. No. 11/535,901, mailed on Apr. 14, 2009, 9 pages.
Notice of Allowance for U.S. Appl. No. 11/535,901, mailed Sep. 21, 2010, 26 pages.
Response to Office Action for U.S. Appl. No. 11/535,901, filed on Oct. 9, 2009. 12 pages.
Office Action for U.S. Appl. No. 11/535,901, mailed on Jun. 9, 2009, 22 pages.
Restriction Requirement for U.S. Appl. No. 11/535,901, mailed on Apr. 14, 2009, 9 pages.
Office Action for U.S. Appl. No. 11/535,901, mailed on Jan. 29, 2009, 22 pages.
Advisory Action for U.S. Appl. No. 11/331,777, mailed on Feb. 17, 2010, 3 pages.
Response to Office Action for U.S. Appl. No. 11/331,777, filed on Feb. 5, 2010, 8 pages.
Office Action for U.S. Appl. No. 11/331,777, mailed on Dec. 8, 2009, 16 pages.
Response to Office Action for U.S. Appl. No. 11/331,777, filed on Aug. 5, 2009, 7 pages.
Response to Advisory Action for U.S. Appl. No. 11/331,777, filed on Mar. 16, 2009, 10 pages.
Advisory Action for U.S. Appl. No. 11/331,777, mailed on Mar. 10, 2009, 3 pages.
Office Action for U.S. Appl. No. 11/331,777, mailed on Oct. 14, 2008, 13 pages.
Response to Office Action for U.S. Appl. No. 11/331,777, filed on Jul. 15, 2008, 8 pages.
Office Action for U.S. Appl. No. 11/331,777, mailed on Apr. 21, 2008, 14 pages.
Response to Office Action for U.S. Appl. No. 11/331,777, filed on Dec. 11, 2008, 8 pages.
Office Action for U.S. Appl. No. 11/331,777, mailed on May 8, 2009, 14 pages.
Office Action for U.S. Appl. No. 11/493,148, mailed on Dec. 17, 2009, 13 pages.
Response to Office Action for U.S. Appl. No. 11/493,148, filed on Sep. 1, 2009, 12 pages.
Response to Office Action for U.S. Appl. No. 11/493,148, filed on Mar. 17, 2010, 13 pages.
Response to Office Action for U.S. Appl. No. 11/493,148, filed on Feb. 19, 2009, 12 pages.
Office Action for U.S. Appl. No. 11/493,148, mailed on Sep. 24, 2008, 14 pages.
Office Action for U.S. Appl. No. 11/493,148, mailed on Mar. 25, 2010, 14 pages.
Office Action for U.S. Appl. No. 11/493,148, mailed on Jun. 5, 2009, 14 pages.
Non-Final Office Action for U.S. Appl. No. 12/983,666, mailed Oct. 6, 2011, 47 pages.
Office Action for EP Application No. 07758616.2, mailed on Jun. 6, 2011, 5 pages.
Leron, et al, "Sacrohysteropexy with Synthetic Mesh for the Management of Uterovaginal Prolapse", British Journal of Obstetrics and Gynaecology, vol. 108, Jun. 2001, pp. 629-633.
"Capio CL Transvaginal Suture Capturing Device," Designed for Transvaginal Suture Fixation to Cooper's Ligament for Sling Procedures, Boston Scientific, 2000, 1 page.
"Capio Open Access and Standard Suture Capturing Devices", Reach, Throw and Capture: One Step, One Device, Boston Scientific, 2006, 2 pages.
"Capio RP Suturing Device" Boston Scientific, 2006, 1 page.
Final Office Action for U.S. Appl. No. 12/983,666, mailed Apr. 24, 2012, 10 pages.
Office Action Response for U.S. Appl. No. 12/983,666, filed Jul. 24, 2012, 2 pages.
Final Office Action Response for U.S. Appl. No. 12/983,666, filed Jun. 25, 2012, 8 pages.

(56) References Cited

OTHER PUBLICATIONS

Non-Final Office Action Response for U.S. Appl. No. 12/983,666, filed Feb. 3, 2012, 9 pages.
International Search Report and Written Opinion for International Application No. PCT/US2011/049753, mailed Mar. 6, 2012, 21 pages.
Non-Final Office Action for U.S. Appl. No. 12/983,666, mailed Jul. 30, 2013, 10 pages.
Non-Final Office Action for U.S. Appl. No. 13/218,840, mailed Jun. 7, 2013, 11 pages.
Non-Final Office Action Response for U.S. Appl. No. 12/983,666, filed Oct. 30, 2013, 8 pages.
Non-Final Office Action Response for U.S. Appl. No. 13/218,840, filed Sep. 3, 2013, 9 pages.
Notice of Allowance for JP Application No. 2009-500607, mailed Jun. 19, 2013, 3 pages.
Office Action Response for JP Application No. 2012-28740, filed Aug. 23, 2013, 18 pages.
Hardiman, et al, "Sacrospinous Vault Suspension and Abdominal Colposacropexy: Success Rates and Complications", Section of Urogynecology, Department of Obstetrics and Gynecology, University of Toronto, Mount Sinai Hospital, Sep. 18, 1995, 5 pages.
Pohl, et al, "Bilateral Transvaginal Sacrospinous Colpopexy: Preliminary Experience", 23rd Annual Meeting of the Society of Gynecologic Surgeons, Feb. 24-26, 1997, 7 pages.
Shah, et al, "Short-Term Outcome Analysis of Total Pelvic Reconstruction With Mesh: The Vaginal Approach", The Journal of Urology, vol. 171, Jan. 2004, pp. 261-263.
Non-Final Office Action for U.S. Appl. No. 11/331,777, mailed Dec. 6, 2013, 18 pages.
Final Office Action for U.S. Appl. No. 11/331,777, mailed Apr. 14, 2014, 18 pages.
Non-Final Office Action Response for U.S. Appl. No. 11/331,777, filed Mar. 6, 2014, 8 pages.
Final Office Action Response for U.S. Appl. No. 13/218,840, filed Mar. 24, 2014, 9 pages.
Final Office Action for U.S. Appl. No. 13/218,840, mailed Dec. 24, 2013, 11 pages.
Notice of Allowance for U.S. Appl. No. 13/218,840, mailed May 1, 2014, 7 pages.
Office Action Response for CA Application No. 2,644,983, filed Mar. 28, 2014, 24 pages.
Office Action for European Patent Application No. 06815573.8, mailed on Nov. 15, 2013, 3 pages.
Response to Office Action for EP Patent Application No. 07758616.2, filed on Oct. 17, 2011, 31 pages.
Office Action for Japan Application No. 2012-28740 (with Translation), mailed Dec. 25, 2013, 7 pages.
International Preliminary Report on Patentability for International Application No. PCT/US11/49753, mailed on Mar. 14, 2013, 9 pages.
Final Office Action for U.S. Appl. No. 12/983,666, mailed on May 30, 2014, 13 pages.
Non-Final Office Action for U.S. Appl. No. 12/983,666, mailed on Aug. 26, 2014, 12 pages.
Advisory Action for U.S. Appl. No. 12/983,666, mailed on Jul. 13, 2012, 3 pages.
Final Office Action for U.S. Appl. No. 13/218,840, mailed on Dec. 24, 2013, 11 pages.
Notice of Allowance for U.S. Appl. No. 13/218,840, mailed on Aug. 15, 2014, 7 pages.
Office Action for Canadian Patent Application No. 2,644,983, mailed on May 26, 2014, 2 pages.
Extended European Search Report for European Patent Application No. 13164488.2, mailed on Jul. 31, 2014, 6 pages.

* cited by examiner

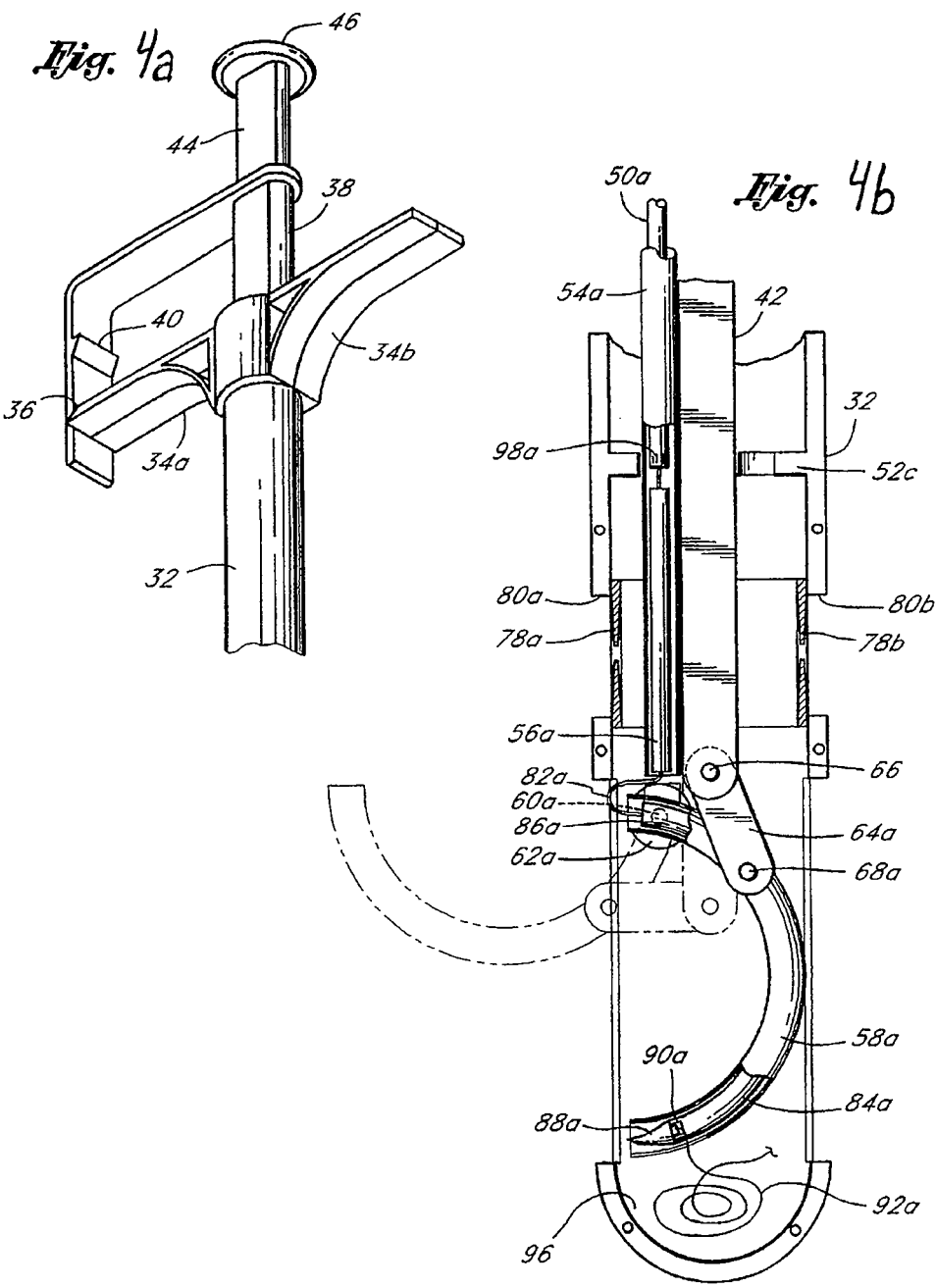

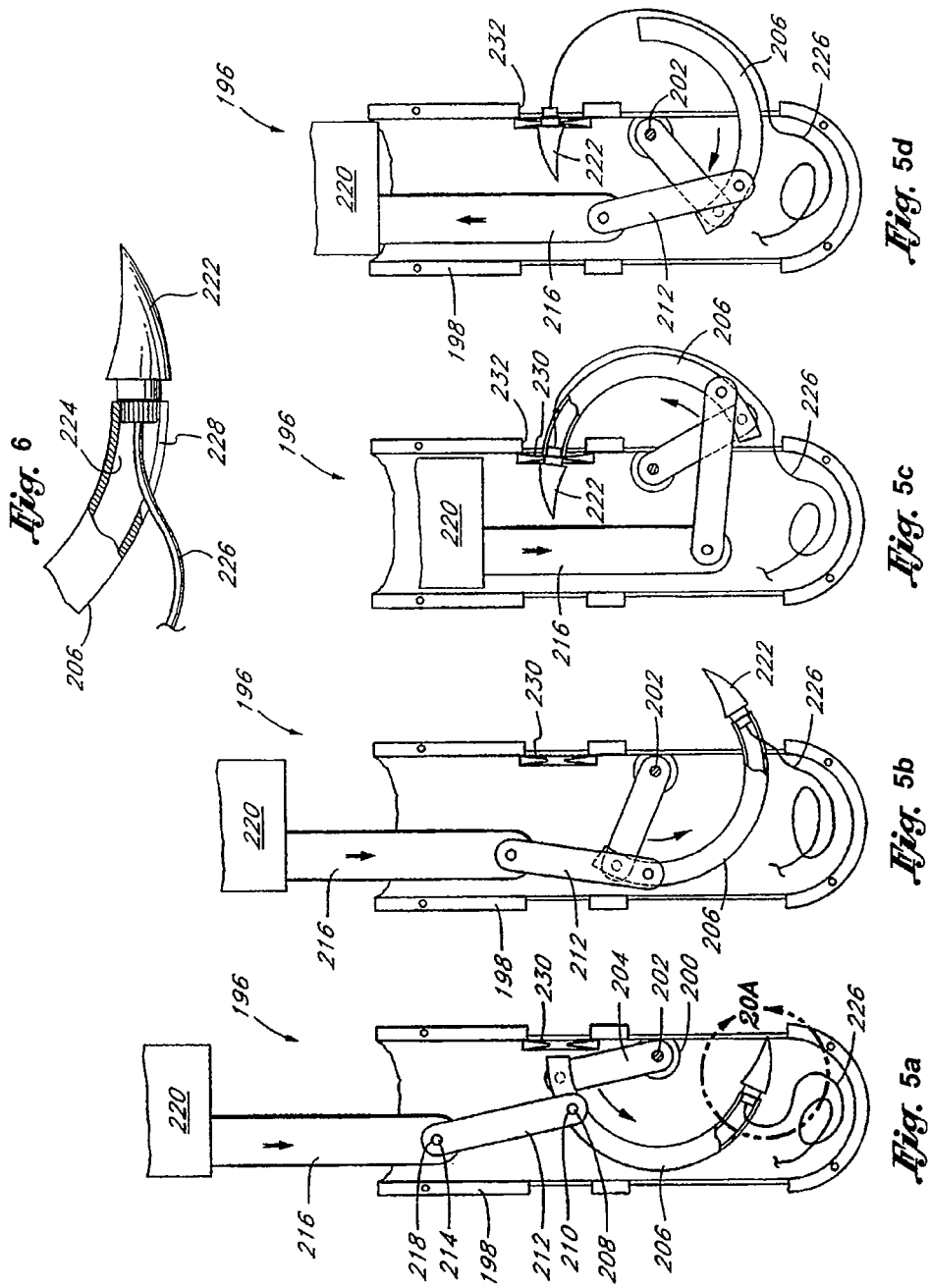

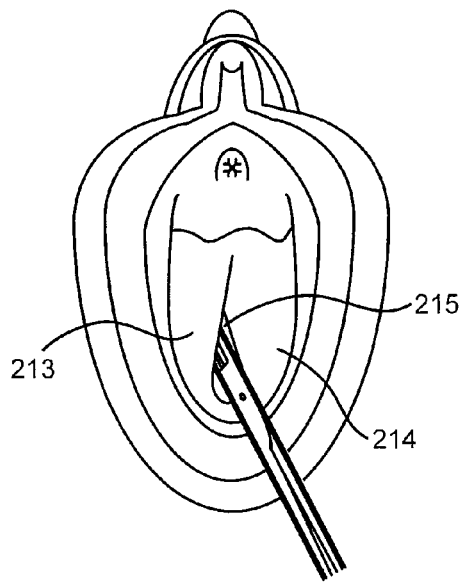
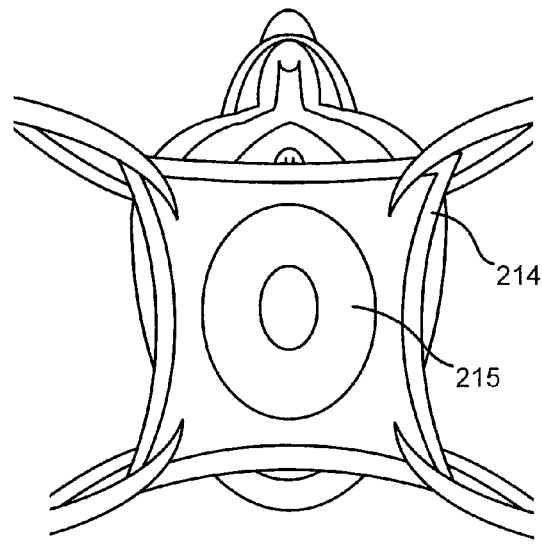
FIG. 7a    FIG. 7b
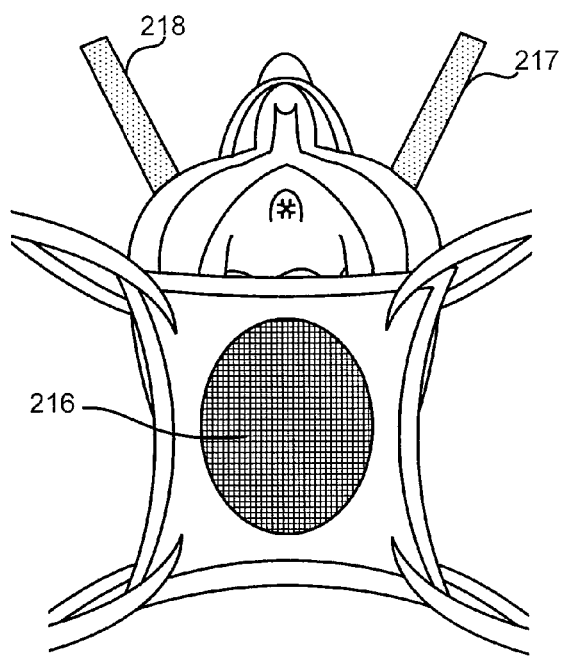
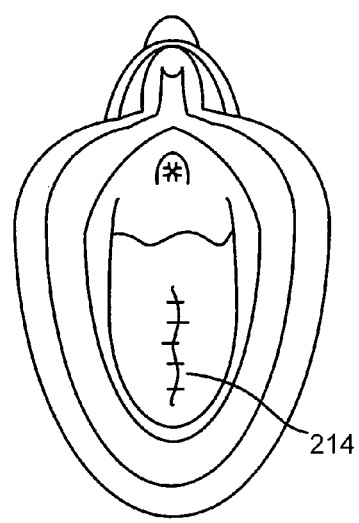
FIG. 7c    FIG. 7d

SYSTEM AND METHOD FOR TREATING TISSUE WALL PROLAPSE

CROSS-REFERENCE TO RELATED APPLICATIONS

This application claims priority from U.S. Provisional Patent Application Ser. No. 60/782,911, filed on Mar. 16, 2006, and U.S. Provisional Patent Application Ser. No. 60/852,932, filed Oct. 19, 2006, both of which are expressly incorporated herein by reference in their entirety.

BACKGROUND OF THE INVENTION

1. Field of the Invention

The present invention relates in general to a system and method in the field of prolapse treatment. More particularly, the present invention relates to an apparatus with multiple components, and a method for surgically correcting tissue wall prolapse using the same. Specifically, one embodiment of the present invention is a kit that has a pre-cut shaped mesh graft, and a graft delivery device.

2. Discussion of the Related Art

As is known to those skilled in the art, the treatment of vaginal wall prolapse has been hampered by high failure rates. Reasons for failure include the inherent weakness of the tissue being re-approximated and the inability of the repair to withstand the forces applied by the abdominal cavity bearing down from above. In the last decade, one advance in repair has been the addition of grafts to reinforce vaginal prolapse repairs. While this technique has gained acceptance, there lacks a consensus regarding how to affix the graft under the vaginal wall to best maintain durability and vaginal caliber.

Some known procedures can cause patient discomfort and/or pain and there is a risk that the graft will become dislodged with time. Additionally, when a graft is sewn into place with standard sutures over the pelvic floor muscles, it may cause pain from suture entrapment. Further, sutures are prone to pullout because the sutures are placed into tissue that is thin and inherently weak. Finally, the placement of the sutures varies among surgeons. Accordingly, it is difficult to teach proper graft placement.

With the introduction of new techniques, improved devices have been made commercially available. In general, these systems utilize medical mesh with wings at the corners so that the mesh may be drawn through the pelvic floor musculature and pelvic ligaments to secure the mesh.

An accepted access point for securing the wings of these systems has been through the obturator membrane and ischiorectal fossa. Access is generally made via these structures because the apex of the vagina is located deep within the pelvis. However, the problem with accessing the apex via these structures is that this anatomy is unfamiliar to surgeons. Further, safety remains a concern for surgeons because these systems require the passage of sharp needles long distances through these unfamiliar anatomic paths with unseen neurovascular structures potentially nearby. Thus, extensive training and anatomy education is required to properly learn the technique.

In general, the embodiments disclosed in the above-referenced patents and publications have the disadvantage that they are difficult or dangerous to use without extensive training. Also, they are only partially effective to treat prolapse. Other disadvantages include increased risk and ineffective results over time. Given these disadvantages, patients suffering prolapse either must wait long periods of time for treatment or forego treatment altogether because of the risk involved and the necessary high-level of surgeon skill. This further leads to a procedure with a relatively high cost.

Therefore, what is needed is a relatively simple apparatus and method for the treatment of vaginal wall prolapse. Specifically, what is needed is an apparatus and method that reduce patient discomfort and that are easily repeatable and highly effective over time.

SUMMARY OF THE INVENTION

The invention disclosed herein includes an apparatus and a method for treatment of vaginal prolapse conditions. The apparatus is a graft having a central body portion with at least one strap extending therefrom. The strap has a bullet needle attached to its end portion and is anchorable to anchoring tissue in the body of a patient. The invention makes use of a delivery device adapted to deploy the graft in a patient. The inventive method includes the steps of making an incision in the vaginal wall of a patient, opening the incision to gain access inside the vagina and pelvic floor area, inserting the inventive apparatus through the incision, and attaching the straps of the apparatus to anchoring tissue in the patient.

BRIEF DESCRIPTION OF THE DRAWINGS

FIGS. 4a and 4b are cut-away views of a portion of the graft placement device of FIG. 3a.

FIGS. 5a, 5b, 5c, and 5d illustrate a side view of a portion of the graft placement device of FIG. 3a and a bullet needle.

FIG. 6 illustrates a side cut-away view of a portion of the graft placement device of FIG. 3a.

FIGS. 7a, 7b, 7c and 7d are schematic illustrations of a vaginal area of a patient.

Figure 1:
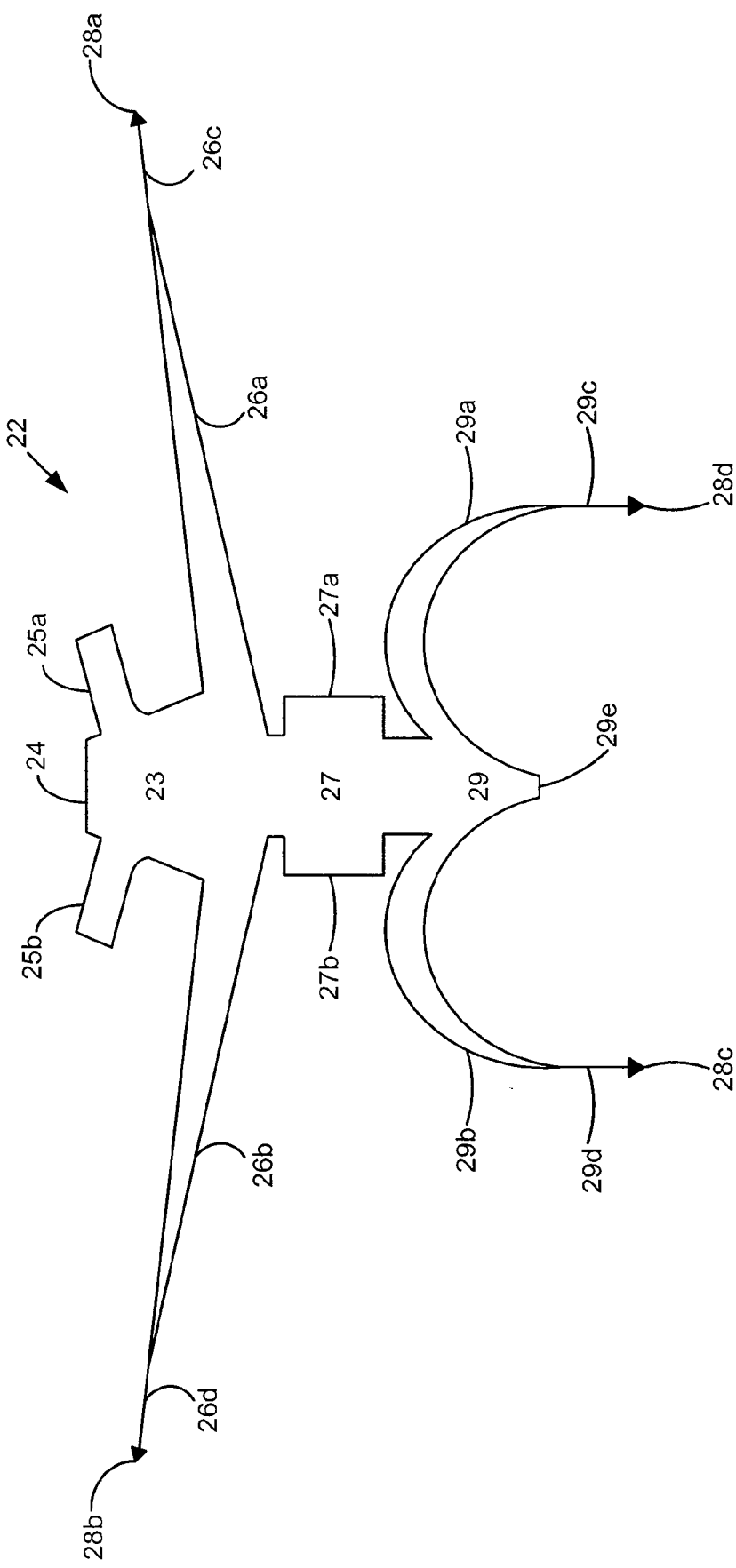
FIG. 1 illustrates a top view of a graft according to an embodiment of the present invention.

In describing the illustrated embodiments of the invention that is illustrated in the drawings, specific terminology may be used for the sake of clarity. However, it is not intended that the invention be limited to the specific terms so selected and it is to be understood that each specific term includes all technical equivalents that operate in a similar manner to accomplish a similar purpose.

DETAILED DESCRIPTION

This invention, which includes elements of a method and device, represents a novel way of treating vaginal wall prolapse. The present invention overcomes the above-mentioned limitations of the art. The invention has two main components: a graft and a graft placement device or delivery device. The graft itself can have several sizes and shapes and be made of a variety of materials. See, e.g., U.S. Pat. Nos. 6,102,921 and 6,638,284 incorporated in their entirety by reference. In one embodiment, a synthetic polypropylene mesh graft version is used. One embodiment of the inventive graft is designed to cover the entire vaginal vault and provide anchoring to the arcus tendineus, the sacrospinous ligament, and/or the levator ani muscle of the patient.

Whereas several known methods use long needles to aid in graft placement (which hamper their adoption), the disclosed apparatus uses a graft that includes bullet needles attached thereto. The bullet needles are configured to attach the graft to the accepted anatomic structures without having to pass through the previously mentioned unfamiliar pathways such as the ischiorectal fossa or the obturator membrane. The graft is, therefore, able to, as a result of its design, reach the desired attachment points directly through the vaginal canal.

The graft may be placed using a placement device or delivery device. One embodiment of the delivery device is a device such as a Boston Scientific Corporation "Laurus™" or "Capio™" device, which can be good a predicate device for the delivery device component of this kit. The graft delivery device acts as a suture-capturing device also but in the disclosed invention the suture can be a mesh wing, such as a strap, arm, or leg.

Using the components described above, in one embodiment, the inventive method includes the following steps: making an incision in the vaginal wall; opening the incision to gain access inside the vagina and Pelvic Floor; taking a suture-capturing device in hand; attaching a mesh wing with a bullet needle to a suture capturing device; inserting the wing, needle and suture device through the incision and inside the vagina; pushing the wing and bullet needle through the ligaments or muscle; pulling the wing back out of the incision with the suture device; releasing the bullet needle and wing from the suture device; attaching another wing and its bullet needle to the suture capturing device, and repeating the process at another location within or through the vagina; repeating the process with the other wings and bullet needles until all of the wings are attached to the commonly accepted apical and lateral support structures. These are generally the sacrospinous ligament, proximal arcus tendineus, and levator ani muscle. This wing securement allows the custom adjustment for each patient, which would not occur with conventional suture fixation. The excess mesh wing material should then be trimmed away and discarded. After the remaining mesh is secured, the incision is closed.

As mentioned above, one embodiment of the present invention has two main components. The first component is a graft. As best shown in FIG. 1, in one embodiment the graft has a unique shape. While the graft 22 can be shaped as shown in FIG. 1, the graft may be of any suitable shape and generally will incorporate a central body portion and at least two longitudinal side portions, e.g., arms. For example, the graft of the present invention may be produced in a substantially oval shape or trapezium shape with extension arms and legs extending away from the central body portion of the graft. The graft can be positioned over the pubocervical fascia and secured via the surrounding ligaments and/or muscles.

In the embodiment illustrated in FIG. 1, the graft 22 has protrusions referred to as arms, legs, and wings (or generally "wings"). The inventive graft 22 includes an upper portion 23, first edge 24, first wing 25a, second wing 25b, third wing 26a, and fourth wing 26b. A central body portion 27, a first arm 27a, and a second arm 27b also make up the graft 22. The graft 22 further includes a lower portion 29, a first leg 29a, a second leg 29b, a third connecting segment 29c, a fourth connecting segment 29d, and a tail 29e. In one embodiment, the mesh does not include wings 25a and 25b.

The inventive wings, legs, and arms are intended to be used for attachment via the arcus tendineus near the ischial spine for the anterior vaginal wall, the sacrospinous ligament for the posterior vaginal wall, and/or the levator ani muscle. These anatomical structures are deep in the pelvis making them excellent for support but otherwise difficult to access without a graft delivery device as will be described more fully below. Once such a device reaches the preferred location, the device helps the surgeon to wedge the graft into place.

In some embodiments, the graft material itself is a synthetic mesh similar to the mesh material made by Boston Scientific Corporation called "POLYFORM™." In other embodiments, a mesh as described in U.S. Patent Application Pub. No. 2005/0261545 or a mesh as described in U.S. Patent Application Pub. No. 2005/0222591, both of which are incorporated by reference in their entirety, is used as the material for the graft. There are also many types of available mesh grafts such as the mesh described in PCT/US 02/31681 to Ethicon, which is also incorporated by reference. One embodiment of a mesh includes a plurality of open pores bounded by strands made of nonwoven polymeric material, for example, a polypropylene having monofilament fibers, wherein the junctions between the strands are without open interstices and the majority of open pores of the mesh have an area of less than 15 mm$^2$. In some embodiments, the pore size has an area of less than 10 mm$^2$. In other embodiments, the pore size of the central body portion of the mesh is greater than the pore size of the longitudinal side portions. In some embodiments, the pore size range in these portions is between 3 mm and 8 mm wide. A mesh according to one embodiment of the invention is also light and very flexible having a weight of less than 0.0080 g cm$^2$. The materials and mesh arrangement are such so as to minimize the chance of infection after implantation.

While any conventional prosthetic material currently used for the treatment of pelvic organ prolapse can be employed when performing the inventive method, there are many so-called biografts that can be used as well such as animal or human donor tissue or any other xenograft material such as pig dermis, bovine dermis, allograft, or homograft of skin. It is important to note that this novel system and method does not preclude using any number of materials as the graft and will be amenable to the use of future materials as they become available. However, while any of the above-mentioned materials are suitable for reinforcing the vaginal wall according to the disclosed method and with the disclosed apparatus, a synthetic polypropylene mesh is preferred.

On each arm and leg, respectively, is a first bullet needle 28a, second bullet needle 28b, third bullet needle 28c, and fourth bullet needle 28d. In one embodiment, the graft 22 also includes a first needle-connecting segment 26c and a second needle-connecting segment 26d.

Figure 2A:
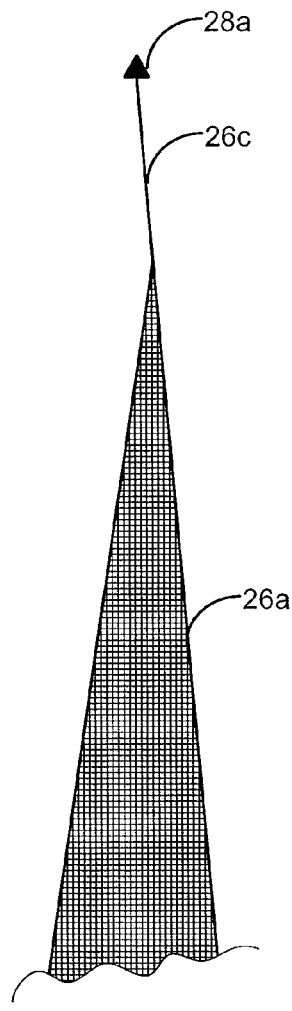
FIGS. 2a, 2b, and 2c illustrate top views of various wings and bullet needles of the graft according to an embodiment the present invention.
Figure 2B:
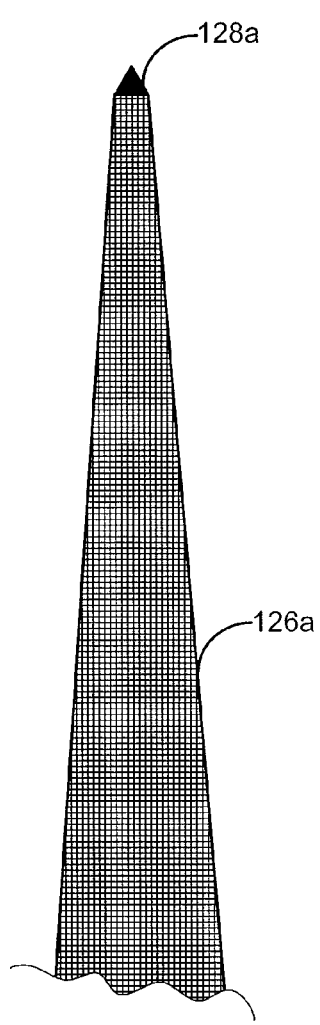
Figure 2C:
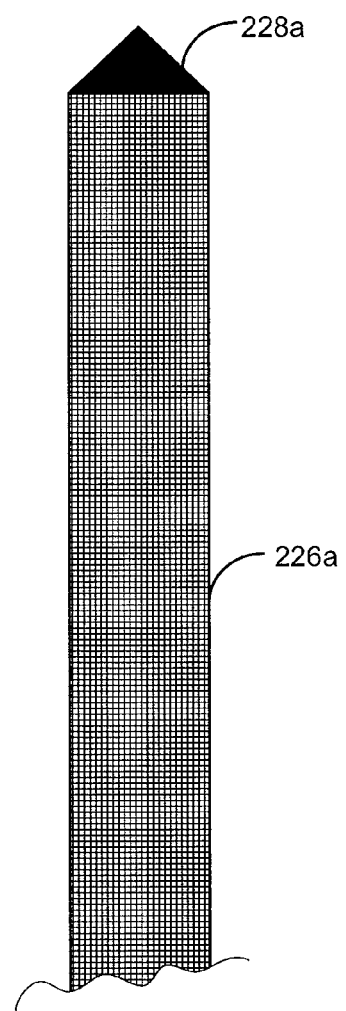

FIGS. 2a-2c show various embodiments of the bullet needle and the leg or arm. In FIG. 2a, for example, the bullet needle 28a is relatively small and generally round and is connected to the arm 26a via a thread or very thin segment of mesh, e.g., by needle-connecting segment 26c. In FIG. 2b, the bullet needle 128a is bigger (than 28a) and is round and is connected to the arm 126a via a segment of mesh. In FIG. 2c, for example, the bullet needle 228a is bigger and flatter (than 28a and 128a) and is connected to the arm 226a via a wider segment of mesh. In one embodiment, the bullet needles may be formed from stainless steel. In another embodiment, the "needle" is formed of the graft material. For example the "needle" could be formed of more dense graft material. In such an embodiment, the stainless steel needles may be replaced altogether.

While in some embodiments the inventive wing, leg, or arm of the graft is affixed to a relatively small rounded bullet needle, in some embodiments the wing, leg, or arm is also tapered to allow atraumatic passage of it through the tissue and promote gripping of the wider portion of the arm or leg to the surrounding tissue. Further, instead of using the needle method for attaching the graft, it is also possible for the graft to be attached by other fastening means. Such fastening means including a medical adhesive or glue, microwave or radio frequency welding, staples, tacks, and a hook and loop type fastener.

One of the novel concepts in the disclosed invention is the adaptation of a previously-patented suture-passing device for the graft delivery device, e.g., as described in U.S. Pat. Nos. 5,364,408; 5,540,704; 5,458,609; 5,575,800, and 5,662,664 all incorporated by reference in their entirety. See also, e.g., U.S. Pat. Application Publication No. 2006/0052801, also incorporated in its entirety by reference. In one embodiment, the disclosed delivery device is based in part on the "Capio™" device, which is sold by Boston Scientific Corp. The Capio™ device was originally patented as the Laurus™ device and is generally used elsewhere for suture passage in limited access cavities. An embodiment of the device is a trocar capped by a curvilinear needle guide and deployable bullet needle that passes to a catch mechanism. A plunger at the other end of the device deploys it.

The disclosed graft can be placed using such a graft delivery device, such as the graft placement device as shown in FIGS. 3a-6, which is the second component of the inventive apparatus. The modification of such a graft placement device allows the surgeon to use this device to pass the graft's wings, e.g., the arms and legs, directly through the desired anchoring structures without having to traverse these pathways. Further, the disclosed graft placement device itself is easier to use than the graft delivery devices currently in use in prolapse surgery. Therefore, the disclosed graft placement device requires less skill to deliver the graft wings to their target locations.

Detailed drawings of an illustrative embodiment of the graft delivery device are shown in FIGS. 3a, 3b, 4a, 4b, 5a-5d, and FIG. 6 wherein the graft delivery device 30 includes an outer housing 32, with finger grips 34a and 34b, and a deployment catch 36. In some embodiments, the outer housing 32 is made of injection molded plastic such as polycarbonate, as are many other of the components described herein. A deployment sleeve 38, slidably disposed within the outer housing 32, has a retention catch 40 and is attached to a pushrod 42, constructed for example, of stainless steel. A driver shaft 44 includes a button 46 and has a hole 48a, into which is bonded an elongate rigid shaft 50a. The rigid shaft 50a, which may be made of music wire, passes through outer housing ribs 52a, 52b, and 52c, and terminates slidably disposed within a hollow cylinder 54a. The hollow cylinders 54a and 54b, which can be made from stainless hypodermic tubing, are held in recesses in the outer housing ribs 52b and 52c. An elongate flexible tubular member 56a, that may be made of polypropylene or other suitable material, is also slidably disposed within the hollow cylinder 54a. As shown in FIG. 4b, needle guide 58a may also be constructed from stainless hypodermic tubing, and has pivot pins 60a and 60b pivotally disposed within outer housing bosses 62a and 62b. A driving link 64a is attached by a link pin 66 to the pushrod 42 and to the needle guide 58a by a pivot pin 68a, with the entire mechanism preferably made of stainless steel so as to maximize the biocompatibility as well as the strength of the actuating members.

Referring again to FIGS. 3a and 3b, the device 30 has a driver retainer 70 that is slidably disposed within the outer housing 32, and is fixably attached to rigid shafts 50a and 50b, with a hole 72 to allow the pushrod 42 to pass slidably therethrough. A driver spring 74, which can be wound from stainless steel wire, is compressed between the driver retainer 70 and the outer housing rib 52b. A deployment spring 76, also made of stainless steel wire is compressed between an end 77 of the deployment sleeve 38 and outer housing rib 52a. A needle catch 78a is housed within a recess 80a in the outer housing 32. Referring now to FIG. 4b, a retraction line 82a that is preferably made of Kevlar™, is slidably threaded through the flexible tubular member 56a and is attached to a needle carrier 84a by means of a crimp 86a or other means that would bind the retraction line 82a to the needle carrier 84a. The distal end of the retraction line 82a is attached to the rigid shaft 50a by means of another crimp 98a or other means.

Figures 3A, 3B:
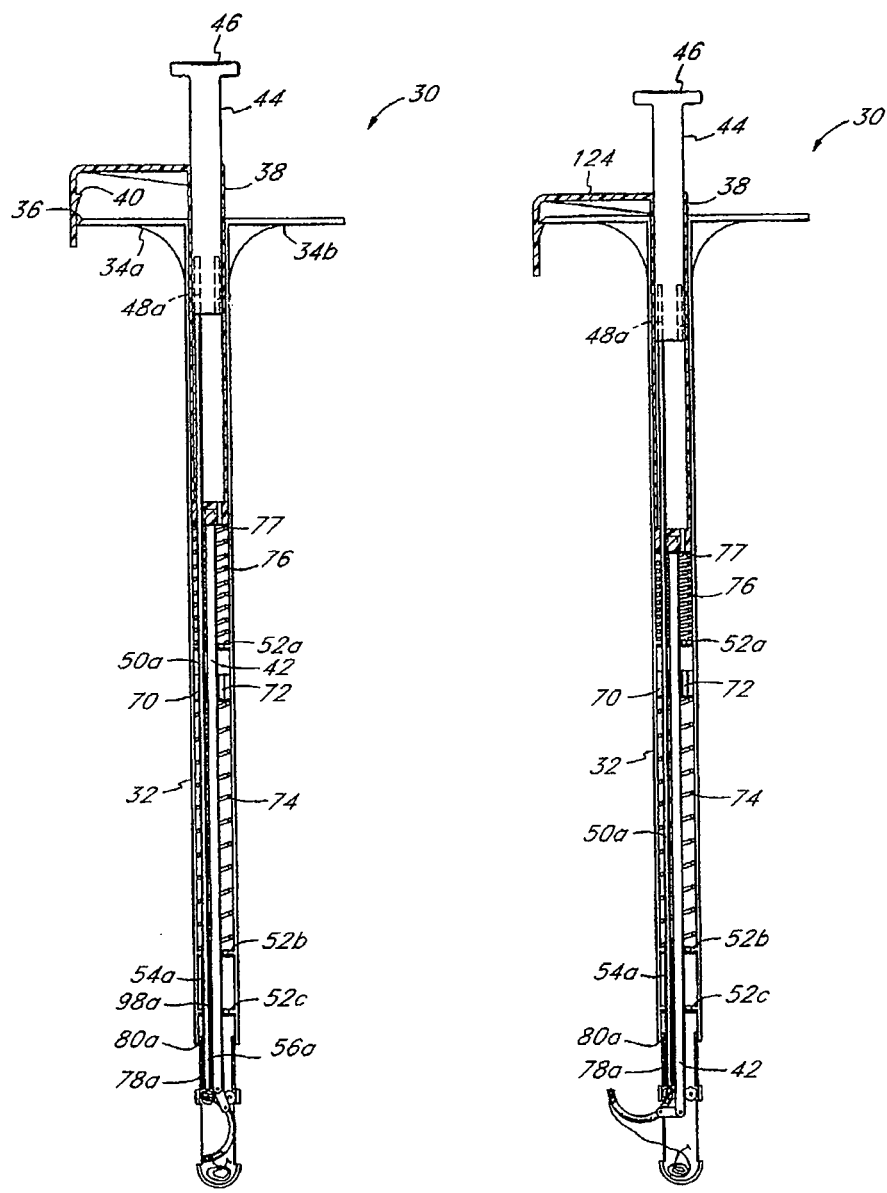
FIGS. 3a and 3b illustrate a side cut away view of a graft placement device.

Referring to FIG. 3b, arm 124 of deployment sleeve 38 is pushed so that the sleeve slides within the outer housing 32, compressing spring 76, and in turn sliding pushrod 42. As illustrated in FIG. 4b, when the pushrod 42 slides relative to the outer housing 32, it forces the needle guide 58a to pivot about the pin 60a that is retained in outer housing boss 62a.

Referring again to FIG. 4b, a retraction line 82a that is preferably made of Kevlar™, is slidably threaded through the flexible tubular member 56a and is attached to a needle carrier 84a by means of a crimp 86a or other means that would bind the retraction line 82a to the needle carrier 84a. The distal end of the retraction line 82a is attached to the rigid shaft 50a by means of another crimp 98a or other means. The needle carrier 84a is slidably disposed within the needle guide 58a, and holds a needle 88a (or e.g. bullet needle 28a), typically constructed of surgical grade stainless steel in a recess 90a, such needle having a suture 92a attached thereto. The suture material is preferably polyglycolic acid, but may be made of polypropylene, nylon, silk, catgut, or any other materials known in the art selected for its biocompatibility and tensile strength to be used in the body for the approximation of tissue. The suture 92a exits the needle guide 58a by means of a groove and is stored in a recess 96 in outer housing 32. In one preferred embodiment, suture 92a would be, e.g., thread 26c which is connected to arm 26a as shown in FIG. 2a.

It should be understood that in the interest of clarity only one half of an embodiment of a graft placement device of the present invention is shown in FIGS. 5a, 5b, 5c, 5d, and 6. The other half is quite similar in function and structure to the half described herein. The upper portion of the device is similar in construction and materials to the previously disclosed embodiments, and is not repeated here. The graft placement device 196 includes an outer housing 198 having bosses 200 into which a pin 202 is rotatably inserted. The pin 202 is secured to an arm 204, which is attached to a needle carrier 206. A pin 208 on needle carrier 206 is rotatably inserted into a hole 210 in a link 212. Another pin 214 is secured to a pushrod 216 and is rotatably inserted into another hole 218 in the link 212. The pushrod 216 is attached to a sleeve 220 slidably disposed within the outer housing 198. FIG. 6 shows a detail view of a needle 222 (similar to bullet needle 28a) held in a recess 224 in the needle carrier 206. A thread 226, like thread 26c, is attached to the needle 222 and is threaded through a slot 228 in the needle carrier 206. In some embodiments all components in this mechanism are constructed of surgical grade stainless steel, chosen for its biocompatibility and strength.

In Use

Using the components briefly described above, a placement method includes the following steps: making an incision in the vaginal wall; opening the incision to gain access inside the vagina and Pelvic Floor; taking a suture-capturing device, such as a graft placement device, in hand; attaching the mesh wing with bullet needle to the suture capturing device, such as a graft placement device; inserting the wing, needle and suture device through the incision and inside the vagina; pushing the wing and bullet needle through the ligaments or muscles; pulling the wing back out of the incision with the suture device; releasing the bullet needle and wing from the suture device; attaching another wing and its bullet needle to the suture device and repeating the process at another location within the vagina; repeating the process with the other wings and bullet needles until all of the wings are attached to some internal structure such as the commonly accepted apical and lateral support structures. These support structures are generally the sacrospinous ligament, the proximal arcus tendineus, and the levator ani muscle. This wing securement allows the custom adjustment for each patient, which would not occur with conventional suture fixation; the wings should then be tightened as necessary so that the graft control body is covering the internal top wall of the vagina. The excess mesh wing material should then be trimmed away and discarded. After the remaining mesh is secured, the vaginal incision is closed.

Use and operation of the disclosed graft placement device will now be described beginning with reference to FIG. 5a. The device 196 is introduced into the abdomen. Sleeve 220 slides within the housing 198 in the direction indicated by the arrow. As shown in FIG. 5b, as the sleeve 220 moves, it pushes the pushrod 216 which causes the link 212 to cause the needle carrier 206, along with the needle 222 and the thread 226, to rotate about the axis defined by the pin 202. Referring to FIG. 5c, it may be seen that the needle 222 is driven into a catch 230 through an opening 232 in the outer housing 198. Accordingly, in reference to FIG. 5d, it is seen that as the pushrod 216 is retracted, the link 212 is also retracted, causing the needle carrier 206 to rotate about the pivot pin 202 and back through the opening 232 into the outer housing 198, the same position as shown in FIG. 5a.

An alternative embodiment mesh delivery device may resemble the device disclosed in U.S. Pat. No. 6,936,952, which is incorporated by reference. As mentioned above, there are specific anatomic structures, deep in the pelvis, typically used for graft fixation, which are chosen due to their advantageous location and resistance to displacement. Nevertheless because these structures are difficult to access, an incision must be made in the vaginal wall. See, e.g., FIGS. 7a and 7b. Once the incision is made, a delivery device such as a graft placement device is used to put a graft in place. The placement device uses a needle, that can be affixed to each one of the mesh arms or legs of the implant. The needle and graft are loaded into a needle guide located on the delivery device. In some embodiments of the inventive method, once the graft and the needle are loaded in the graft placement device, the remainder of the body of the graft with the remaining arms and legs hangs from the needle. After the appropriate dissection of the paravaginal tissue is made and the anchoring structures are located and cleared of any connective tissue, the graft placement device is moved into place over the desired structure. The plunger is then compressed and the needle deployed. Once the needle and mesh pass through the desired anchoring structure, the entire device is gently retracted out of the vagina. This leaves the arm or leg of the graft loosely encircling the anchoring point. The delivery device is then again held in position to engage the subsequent needles from each of the remaining needles passing each wing around its respective anchoring point. The graft can be delivered as a single piece or cut into two separate pieces for delivery into the anterior and posterior wall of the vagina separately. The arm or leg can then be adjusted. This is done by pulling the graft as cephalad as necessary causing the graft to lie flat in its respective compartment. The ends of each arm or leg are then cut to release the needle. The excess mesh and needle are then disposed of.

Figure 8:
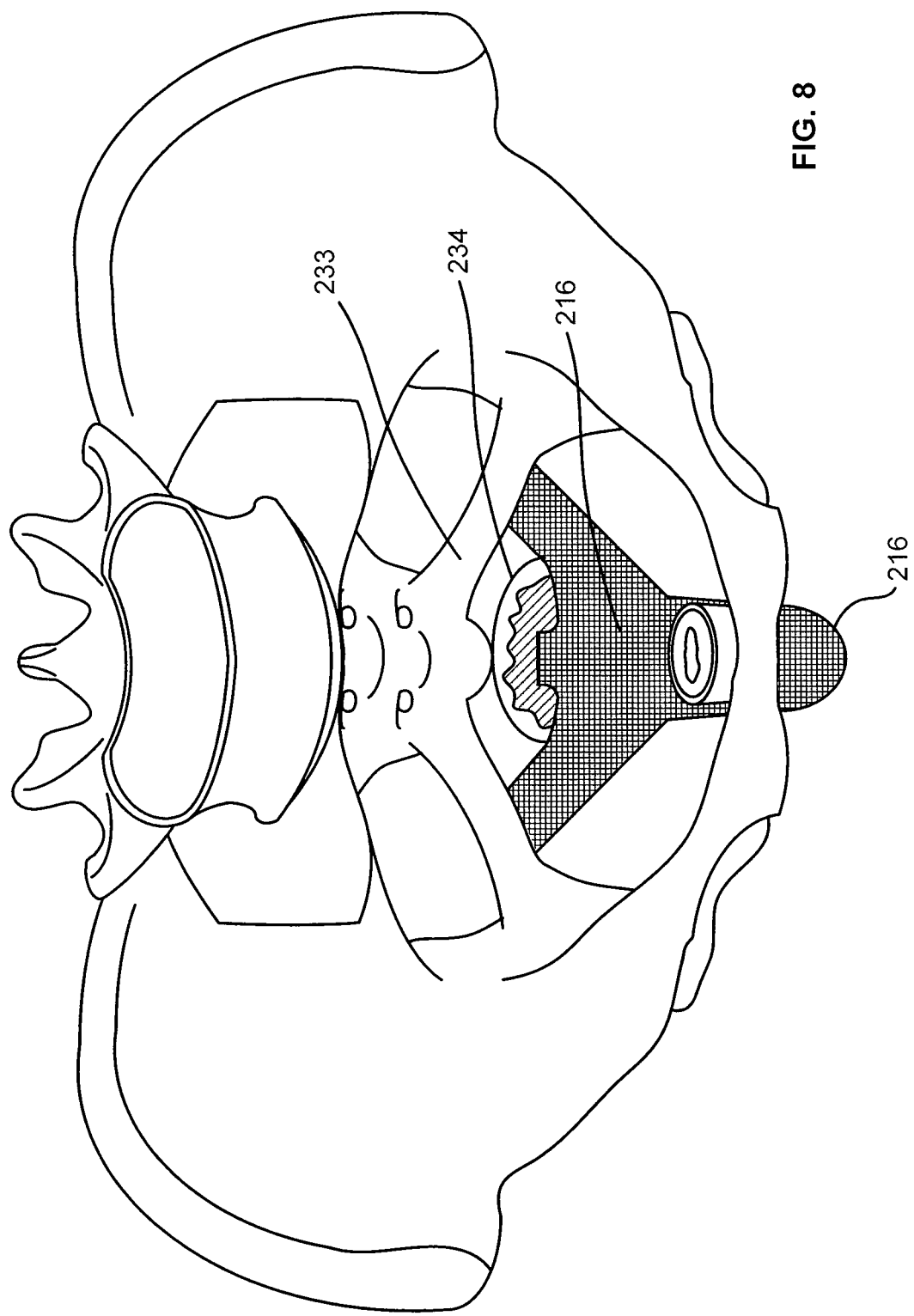
FIG. 8 is a schematic illustration of various parts of the female anatomy with some components of the present invention in place.

Turning to FIG. 7a, posterior vaginal wall 213 is shown with the epithelium 214 of the posterior vaginal wall in place. In one embodiment of the inventive method, a longitudinal incision is performed in order to mobilize the epithelium 214 off the underlying fascia 215. Dissection is carried out laterally to the levator ani muscles on each side. In the upper part of the vagina, dissection is continued in a lateral and cranial direction through the rectal pillars on both sides towards the sacrospinous ligaments on each side. This creates a safe space through which to deploy the device, and forms bilateral tunnels from the posterior vaginal wall dissection to each sacrospinous ligament. The fascia of the recto-vaginal septum can be plicated (not shown). As illustrated in FIG. 7c, a graft, e.g. graft 216 designed for a posterior vaginal wall repair is placed over the recto-vaginal septum fascia 215 with each extension arm 217, 218 placed into the tunnel extending from the posterior vaginal wall dissection to the sacrospinous ligament. After the remaining mesh is secured, the vaginal incision is closed, as illustrated in FIG. 7d. The positioning of the graft 216 is depicted in FIG. 8, which shows its location relative to the sacrospinous ligament 233, the rectum 234 and the vagina 235. In other embodiments, similar methods can be used to access and attach the graft to the levator ani muscle.

The device and method described here can also be implemented with other modifications that allow it to be performed in conjunction with other procedures such as uterine preservation procedures.

While the preferred embodiments and best modes of utilizing the present invention have been disclosed above, other variations are also possible. For example, the materials, shape and size of the components may be changed. Various alternatives are contemplated as being within the scope of the following claims that particularly point out and distinctly claim the subject matter regarded as the invention.

What is claimed is:

1. A method of treating pelvic conditions, comprising:
   making an incision in a vaginal wall of a patient;
   inserting a graft into a body of the patient through the incision, the graft having a central portion, the graft including a first wing, a second wing, and a third wing, the first wing extending from the central portion at an acute angle with respect to a longitudinal axis of the central portion, and a bullet needle connected to the first wing, the first wing extending from the central portion between an upper edge of the graft and a lower edge of the graft, the first wing being formed of a mesh material, the graft includes a thread formed from polyglycolic acid and being disposed between the bullet needle and the first wing, the first wing being disposed between the second wing and the third wing, the first wing having a length that is greater than a length of the second wing;
   pushing the first wing and the bullet needle through an arcus tendineus of the patient using a graft placement device such that the first wing enters the arcus tendineus at a first location and exits the arcus tendineus at a second location;
   catching, after the pushing, the bullet needle using the graft placement device; and
   positioning the graft within the body of the patient such that a first portion of the central portion is disposed adjacent an anterior wall of a vagina of the patient.

2. The method of claim 1, further comprising pulling, after the catching, the first wing back out of the incision using the graft placement device such that a portion of the first wing extends through the arcus tendineus.

3. The method of claim 1, further comprising releasing the bullet needle and the first wing from the graft placement device.

4. The method of claim 1, further comprising suturing the incision closed.

5. The method of claim 1, wherein making the incision comprises dissection of paravaginal tissue by pulling back muscle and flesh.

6. The method of claim 1, further comprising loading the bullet needle into the graft placement device such that a remainder of the graft hangs from the graft placement device, the bullet needle being attached to a terminus of the first wing.

7. The method of claim 1, further comprising trimming away excess wing material.

8. The method of claim 1, further comprising adjusting the graft by pulling the central portion to cause the central portion to lie substantially flat in its respective vaginal compartment.

9. The method of claim 1, wherein the graft includes a needle connecting segment disposed between the first wing and the bullet needle, the needle connecting segment has a single tapered portion.

10. The method of claim 1, wherein the positioning the graft includes positioning the graft such that a second portion of the central portion is disposed adjacent a posterior wall of the vagina of the patient.

11. The method of claim 1, wherein the first wing is being disposed between the second wing and the lower edge of the graft.

12. An apparatus for treatment of pelvic conditions, comprising:
a graft having an upper edge, a lower edge, and a central portion disposed between the upper edge and the lower edge, the graft including a first wing, a second wing, and a third wing, the first wing extending from the central portion, the first wing being formed of a mesh material, the central portion defining a longitudinal axis, the first wing extending from the central portion at an acute angle with respect to the longitudinal axis, the first wing extending from the central portion between the upper edge and the lower edge, the first wing being anchorable to anchoring tissue and having an end portion, the first wing being disposed between the second wing and the lower edge, the first wing having a length greater than a length of the second wing, the first wing being disposed between the second wing and the third wing; and
a bullet needle coupled to the end portion of the first wing, the bullet needle configured to be deployed through the anchoring tissue and secured within a catch portion of a delivery device after being deployed through the anchoring tissue, the second wing being devoid of a bullet needle,
wherein the central portion further comprises:
an upper portion disposed adjacent the upper edge, the upper portion having a first side edge extending from a first end of the upper edge substantially towards the central portion, and a second side edge extending from a second end of the upper edge substantially towards the central portion;
a lower portion disposed adjacent the lower edge, the lower portion having a first side edge and a second side edge, the first side edge of the lower portion and the second side edge of the lower portion being oblique to the longitudinal axis such that the first side edge of the lower portion and the second side edge of the lower portion converge toward the lower edge;
the central portion disposed between the upper portion and lower portion, and
the third wing extending from the central portion between the first side edge of the upper portion and the first side edge of the lower portion,
wherein an acute angle of the third wing with respect to the longitudinal axis is different than the acute angle of the first wing with respect to the longitudinal axis, and
a fourth wing and a fifth wing extending from the central portion between the second side edge of the upper portion and the second side edge of the lower portion,
wherein an acute angle of the fifth wing with respect to the longitudinal axis is different than an acute angle of the fourth wing with respect to the longitudinal axis.

13. The apparatus of claim 12, wherein the graft is made from polypropylene mesh.

14. The apparatus of claim 12, wherein the graft is sized and shaped to cover an entire vaginal vault of a patient.

15. The apparatus of claim 12, wherein the first wing is configured to be anchorable to sacrospinous ligaments of the patient.

16. The apparatus of claim 12, wherein the first wing is configured to be anchorable to an arcus tendineus of the patient.

17. The apparatus of claim 12, wherein the first wing is formed of a material and the bullet needle is formed from the material of the first wing.

18. The apparatus of claim 12, wherein the graft comprises a mesh having a plurality of open pores bounded by nonwoven polymeric fibers, and wherein a majority of the open pores of the central portion are larger than a majority of the open pores of the first wing.

19. The apparatus of claim 12, wherein:
the graft is made from a material; and
the bullet needle is formed from the material and is an integral portion of the graft.

20. The apparatus of claim 12, wherein the first wing is tapered such that a width of the first wing monotonically decreases from the central portion of the first wing to the end portion of the first wing.

21. The apparatus of claim 12, wherein:
the central portion has a width; and
the first wing has a width narrower than the width of the central portion.

22. The apparatus of claim 12, wherein:
the third wing extends from the central portion, the third wing being anchorable to anchoring tissue,
the fourth wing is anchorable to anchoring tissue, and
the fifth wing is anchorable to anchoring tissue,
the apparatus further comprising:
a second bullet needle connected to the third wing, the second bullet needle configured to be deployed through anchoring tissue and secured within a catch portion of a delivery device within the body of the patient;
a third bullet needle connected to the fourth wing, the third bullet needle configured to be deployed through anchoring tissue and secured within a catch portion of a delivery device within the body of the patient; and
a fourth bullet needle connected to the fifth wing, the fourth bullet needle configured to be deployed through anchoring tissue and secured within a catch portion of a delivery device within the body of the patient.

23. The method of claim 12, wherein the central portion and the first wing are formed of a mesh material.

24. The apparatus of claim 12, further comprising a suture extending between the first wing and the bullet needle.

25. The apparatus of claim 12, wherein the third wing extends from the central portion at the acute angle with respect to the longitudinal axis.

26. The apparatus of claim 12, wherein the first wing includes a single tapered portion.

27. The apparatus of claim 12, further comprising:
a needle connecting segment disposed between the first wing and the bullet needle, the needle connecting segment having a tapered shape.

28. The apparatus of claim 12, wherein the central portion includes a first portion and a second portion, at least one of the first portion is configured to be disposed adjacent an anterior wall of a vagina of a patient, and the second portion is configured to be disposed adjacent a posterior wall of the vagina of the patient.

29. The apparatus of claim 12, wherein the central portion is disposed a distance from the upper edge and is disposed a distance from the lower edge.

30. The apparatus of claim 12, wherein the third wing is disposed between the first wing and the lower edge and extending from the central portion.

31. The apparatus of claim 12, wherein:
the first wing extends from the central portion between the first side edge of the upper portion and the first side edge of the lower portion,
the acute angle of the first wing with respect to the longitudinal axis is oriented towards the upper edge such that the first wing extends away from the central portion in a general direction of the upper edge; and
an acute angle of the second wing with respect to the longitudinal axis is oriented towards the upper edge such that the second wing extends away from the central portion in the general direction of the upper edge.

32. The apparatus of claim 12, wherein the first wing extends linearly from the central portion.

33. A method of treating pelvic conditions, comprising:
making an incision in a vaginal wall of a patient;
inserting a first graft into a body of the patient through an anterior portion of the vaginal wall of the patient, the first graft having a central portion, the first graft including a first wing, a second wing, and a third wing, the first wing extending from the central portion, and a bullet needle, the bullet needle being directly connected to the first wing, the first wing extending from the central portion between an upper edge of the first graft and a lower edge of the first graft, the first wing being formed of a mesh material, the first wing being disposed between the second wing and the third wing, the first wing having a length that is greater than a length of the second wing;
pushing the first wing and the bullet needle through an arcus tendineus of the patient using a graft placement device such that the first wing enters the arcus tendineus at a first location and exits the arcus tendineus at a second location;
catching, after the pushing, the bullet needle using the graft placement device; and
positioning the first graft within the body of the patient such that a portion of the central portion of the first graft is disposed adjacent the anterior wall of a vagina of the patient;
inserting a second graft through a posterior portion of the vaginal wall of the patient, the second graft having a central portion, at least one wing extending from the central portion, and a bullet needle connected to the at least one wing, the at least one wing being formed of a mesh material;
pushing the at least one wing and the bullet needle of the second graft through bodily tissue using a graft placement device such that the at least one wing of the second graft enters the bodily tissue at a first location and exits the bodily tissue at a second location; and
catching, after the pushing, the bullet needle of the second graft using the graft placement device.

34. The method of claim 33, further comprising:
positioning the second graft such that a portion of the central portion of the second graft is disposed between a rectum of the patient and the vagina of the patient.

35. The method of claim 33, further comprising:
trimming excess material of the at least one wing of the second graft.

36. The method of claim 33, wherein the bodily tissue is a sacrospinous ligament of the patient.

37. The method of claim 33, wherein the central portion of the second graft defines a longitudinal axis, the at least one wing of the second graft extending from the central portion of the second graft at an acute angle with respect to the longitudinal axis of the central portion of the second graft.

* * * * *